US006867045B1

(12) United States Patent
Griffin et al.

(10) Patent No.: US 6,867,045 B1
(45) Date of Patent: Mar. 15, 2005

(54) METHOD FOR DIAGNOSIS OF THROMBOTIC DISORDERS

(75) Inventors: John H. Griffin, Del Mar, CA (US); Samuel I. Rapaport, La Jolla, CA (US); Dzung T. Le, San Diego, CA (US)

(73) Assignees: The Scripps Research Institute, La Jolla, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/606,779

(22) Filed: Jun. 28, 2000

Related U.S. Application Data

(60) Continuation of application No. 09/189,343, filed on Nov. 10, 1998, now Pat. No. 6,083,757, which is a continuation of application No. 08/993,664, filed on Dec. 18, 1997, now Pat. No. 5,834,223, which is a division of application No. 08/339,828, filed on Nov. 14, 1994, now Pat. No. 5,705,395.

(51) Int. Cl.[7] ............................................. G01N 33/86
(52) U.S. Cl. ............................. 436/69; 435/13; 436/86
(58) Field of Search ............................. 435/13; 436/69, 436/86

(56) References Cited

U.S. PATENT DOCUMENTS

| | | | |
|---|---|---|---|
| 5,051,357 A | 9/1991 | Hassouna ..................... 435/13 |
| 5,169,786 A | 12/1992 | Carroll et al. ................. 436/69 |
| 5,198,534 A | * 3/1993 | Steinbuch et al. ........... 530/381 |
| 5,443,960 A | 8/1995 | Dahlback ..................... 435/13 |
| 5,472,852 A | 12/1995 | Smirnov et al. .............. 435/13 |

FOREIGN PATENT DOCUMENTS

| | | |
|---|---|---|
| WO | WO9310261 | 5/1993 |
| WO | 94/17415 | * 8/1994 |

OTHER PUBLICATIONS

The Merck Index, Eleventh Edition, Merck & Co., Inc., 1989, pp. 735 & 1583.*
Physicians' Desk Reference, 48th Edition, pp. 894 & 2538, 1994.*
Dahlback et al, Proc. Natl. Acad. Sci., USA, 91, 1396–1400, 1994.*
Griffin, John H. et al, , "Anticoagulant Protein C Pathway Defective in Majority of Thrombophilic Patients," *Blood,* vol. 82, No. 7, pp. 1989–1993, 1993.
Blood Coagulation Factor Va Abnormality Associated with Resistance to Activated Protein C in Venous Thrombophilia, Sun et al., *Blood,* No. 11, 83:3120–3125, Jun. 1, 1994.
Familial thrombophilia due to a previously unrecognized mechanism characterized by poor anticoagulant response to activated protein C: Predicition of cofactor . . . , Dahlback, et al., *Proc. Natl. Acad. Sci. USA, 90*:10004–1008, 2/93.
Multicenter Evaluation of a Kit for Activated Protein C Resistance on Various Coagulation Instruments Using Plasmas from Health Individuals, Rosen, et al., *Thrombosis and Haemostasis,* No. 2, 72:255–260, 1994.
Diagnosis of activated protein C resistance (factor V Leiden), Baker, et al., *The Lancet, 44*:162, Oct. 22, 1994.
Modified test for activated protein C resistance, Noel W. Preston, *The Lancet, 44*:162–163, Oct. 22, 1994.
COATEST—APC Resistance, Chromogenix AB, Sweden.
Greengard et al., *The New England Journal of Medicine,* vol. 33, No. 23, Dec. 8, 1994, pp. 1559–1562.
Bertina et al., *Nature,* vol. 369, May 5, 1994, pp. 64–67.
Voorberg et al. *The Lancet,* vol. 343, Jun. 18, 1994, pp. 1535–1536.
Legnani et al. *The Lancet,* vol.. 343 Feb. 26, 1994, pp. 541–542.
Zoller et al. *The Lancet* vol. 343, Jun. 18, 1994, pp. 1536–1538.

* cited by examiner

*Primary Examiner*—David Saunders
(74) *Attorney, Agent, or Firm*—Gray Cary Ware & Freidenrich, LLP

(57) ABSTRACT

The present invention provides an in vitro method useful for the diagnosis of a thrombotic disorder in a subject, having or at risk of having the disorder. Specifically, the disorder exemplified herein is associated with APC resistant Factor V and Va. The clotting time of a test sample is analyzed in the presence and absence of APC and compared with a standard reference sample in order to diagnose the subject.

19 Claims, 5 Drawing Sheets

METHOD FOR DIAGNOSIS OF THROMBOTIC DISORDERS

This application is a continuation and claims the benefit of priority under 35 USC § 120 of U.S. application Ser. No. 09/189,343, filed Nov. 10, 1998, now U.S. Pat. No. 6,083,757; which is a continuation of U.S. application Ser. No. 08/993,664, filed Dec. 18, 1997, now U.S. Pat. No. 5,834,223; which is a divisional of U.S. application Ser. No. 08/339,828, filed Nov. 14, 1994, now U.S. Pat. No. 5,705,395. The disclosures of the prior applications are considered part of and are incorporated by reference in their entirety in the disclosure of this application.

BACKGROUND OF THE INVENTION

1. Field of the Invention

This invention relates generally to the field of hematology and blood coagulation disorders and specifically to a method of diagnosing and screening subjects for a thromboembolic disorder.

2. Description of Related Art

In 1993, Dahlback and coworkers (Dahlback, et al., Proc. Natl. Acad. Sci. USA, 90:1004, 1993), described a previously unrecognized mechanism for familial thromboembolic disease characterized by a failure of activated protein C (APC) to appropriately prolong the activated partial thromboplastin time (APTT) of plasma. Inadequate APC-induced prolongation of the APTT was subsequently found in remarkably high prevalence in cohorts of patients with thromboembolic disease (Griffin, et al., Blood, 82:1989, 1993; Koster, et al., Lancet, 342:1503, 1993; Svensson and Dahlback, N. Engl. J. Med., 330:517, 1994), and family studies established its autosomal dominant mode of transmission (Koster, supra; Svensson, supra). Soon thereafter, Dahlback and Hildebrand (Dahlback and Hildebrand, Proc. Natl. Acad. Sci. USA, 91:1396, 1994), reported that APC resistance stemmed from an abnormality of the factor V (FV) molecule.

Bertina, et al. and Greengard, et al. (Bertina, et al., Nature, 369:64, 1994; Greengard, et at., Lancet, 343:1361, 1994), first identified the molecular basis for the FV abnormality. The phenotype of APC resistance was shown to be associated with heterozygosity or homozygosity for a single point mutation in the FV gene that resulted in the substitution of arginine at amino acid residue 506 with glutamine (FV R506Q). This R506Q mutation prevents APC from cleaving a peptide bond at Arg-506 in FV that is required to inactivate factor Va (Bertina, supra; Sun, et al., Blood, 83:3120, 1994).

Because APC-resistant FV appears to be the most prevalent cause of inherited thrombophilia, a reliable, rapid coagulation test that can be used in a variety of circumstances is needed to evaluate a patient with a personal or family history of thrombosis. To date, detection of APC resistance has been based upon obtaining the ratio of the clotting time of the APTT test when plasma is clotted in the presence of calcium ions plus APC to the clotting time of the APTT test when plasma is clotted in the presence of calcium ions alone (APC ratio). The test is considered positive if the APC ratio of a test sample falls below the is range established for a control population.

With increasing use of this test, it became apparent that careful standardization was of utmost importance to obtain consistent and reproducible results (Svensson, supra). For example, it is reported that activation of platelets during the preparation of platelet poor plasma (Cooper, et al., British Soc. for Haematology, 33, 1994), and the use of frozen and thawed plasma (Girolami, et al., Lancet, 343:1288, 1994; Jones and Winter, British Soc. for Haematology, 32, 1994), can alter test results. Moreover, the test cannot be used on plasma from two important groups of patients: patients taking oral anticoagulants, such as warfarin (Svensson, supra), and patients using a lupus anticoagulant (Bokarewa, et al., Blood Coagul Fibrinolysis, 5:37, 194; Hampton, et al., N. Engl. J. Med., 331:130, 1994).

Although it has been recognized that there are thromboembolic disorders that can be diagnosed by the addition of activated Protein C to a patient sample containing coagulation factors and measurement of an enzyme activity that is influenced by the APC added, such disorders are not related to a factor Va or VIIIa that is resistant to degradation by APC (Dahlback, WO93/10261). In addition, this test does not include methodology for testing the two groups of patients described above, e.g., patients taking oral anticoagulants, such as warfarin, and patients using a lupus anticoagulant.

Because of the limitations in the art, there is a need for a specific coagulation test for detecting APC-resistant FV or FVa. The present invention fulfills this need and overcomes many of the problems associated with the prior art tests. The assay of the present invention is based upon a one-stage tissue factor-dependent FV assay in which the clotting time of a test sample is measured when clotting is initiated with calcium alone and when clotting is initiated with calcium plus APC. The test requires no special handling of plasma, can be performed on frozen and thawed plasma, and can be used with any patient in whom testing FV resistant APC is indicated, regardless of their current therapeutic regimen (e.g., warfarin, herparin).

SUMMARY OF THE INVENTION

The present invention provides a novel and specific coagulation test for the detection of APC-resistant factor V or Va. The test is based on a one-stage procoagulant-dependent factor V assay in which the clotting time of a test sample is measured after coagulation is initiated. The test is useful for both subjects having and subjects at risk of having a thormbotic disorder, e.g., thrombophilia.

The present invention provides an in vitro method for diagnosing a subject having or at risk for having a thrombotic disorder associated with activated protein C (APC) resistant factor V or Va comprising contacting a first test sample comprising a coagulation factor containing specimen from the subject, a procoagulant reagent and factor V deficient plasma, with calcium and APC; contacting a second test sample comprising a coagulation factor containing specimen from the subject, a procoagulant reagent and factor V deficient plasma with calcium; and analyzing the clotting times for the first and second test samples. Preferably, the procoagulant reagent is tissue factor and contains a phospholipid reagent.

BRIEF DESCRIPTION OF THE DRAWINGS

FIG. 1 shows primary and secondary plots obtained on FV assay with and without APC of dilutions of normal pooled reference plasma.

DETAILED DESCRIPTION OF THE INVENTION

Figure 1A:
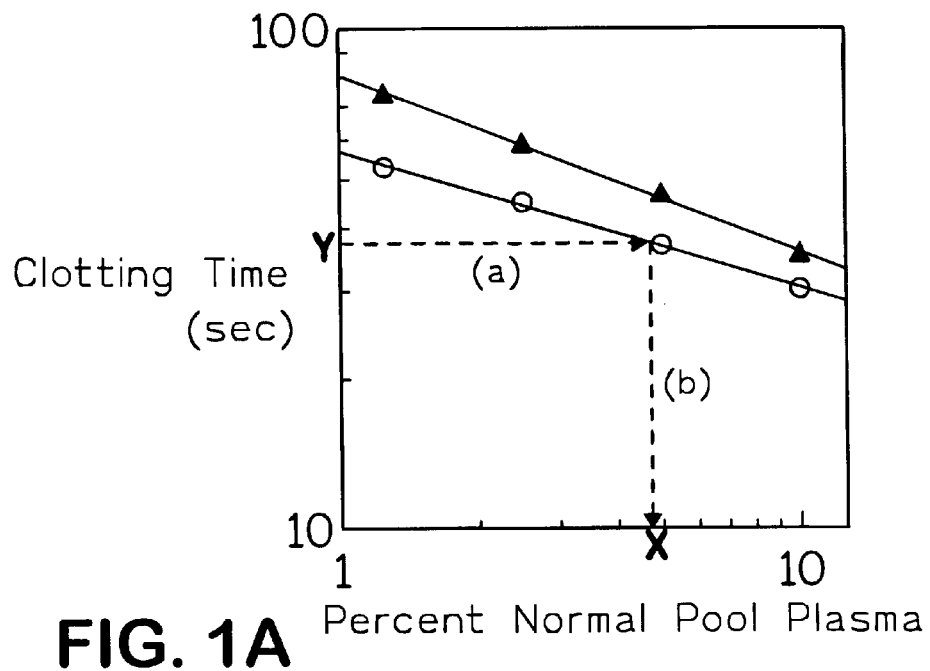
FIG. 1A shows reference curves obtained by plotting the log of clotting times against log of percent concentration of pooled normal reference plasma (primary plot) for the FV assay performed with (▲) and without (○) APC. (Y) a hypothetical clotting time obtained with a test sample which is converted to an equivalent dilution (X) of pooled normal reference plasma via steps (a) and (b).

The present invention provides a novel procoagulant reagent-dependent factor V coagulation assay based on the APC-dependent difference in clotting times of a test sample. The assay is useful for distinguishing among normal subjects and subjects which are heterozygotic or homozygotic for APC resistant FV.

In a first embodiment, the invention provides an in vitro method for diagnosing a subject having or at risk for having a thrombotic disorder associated with activated protein C (APC) resistant factor V or Va comprising contacting a first test sample comprising a coagulation factor containing specimen from the subject, a procoagulant reagent and factor V deficient plasma, with calcium and APC; contacting a second test sample comprising a coagulation factor containing specimen from the subject, a procoagulant reagent and factor V deficient plasma, with calcium; and analyzing the clotting times for the first and second test samples. Preferably the subject is a human.

The method of the invention is useful for diagnosis of subjects having a thrombotic disorder associated with APC resistant factor V or Va as well as those subjects at risk for such disorders. Those at risk for such a disorder include subjects with a family history of thrombosis, pregnant women, septicemic patients, subjects having antiphospholipid antibody syndrome (e.g., lupus anticoagulant antibodies, anticardiolipin antibodies) and patients undergoing surgery, for example.

The term "thrombotic disorder" as used herein refers to a disorder characterized by a blood clot in a broken or an unbroken vessel. The clot itself is referred to as a thrombus. A thrombotic disorder includes, but is not limited to, a thromboembolic disorder, wherein a blood clot or piece of a clot is broken off and transported by the bloodstream to another site, potentially impairing circulation. A thrombotic disorder also includes hereditary and non-thrombophilia (disorders of systemic hemostasis predisposing to thrombosis).

The genotype of APC resistant factor V or Va is most frequently a single point mutation in the FV gene wherein arginine at amino acid residue position 506 is substituted with glutamine. This R506Q mutation prevents APC from normally cleaving a peptide bond at R506 which is required for inactivation of factor Va. The phrase "thrombotic disorder associated with APC resistant factor V or Va", therefore, refers to a thrombotic disorder as defined above, wherein the disorder is at least in part caused by or complicated by a point mutation in FV or FVa that causes APC-resistance.

A coagulation factor-containing specimen utilized as a test sample in the method of the invention may be any specimen containing the factors in question and is preferably a plasma sample. A "procoagulant reagent" as used herein refers to any reagent capable of initiating or stimulating clot formation. A procoagulant reagent of the invention includes any activator of the intrinsic coagulation pathway, such as a clotting factor selected from the group consisting of factor Xa, factor IXa, factor XIa and factor XIIa. Other procoagulant reagents which activate the system via the intrinsic pathway include kallikrein, an APTT (activated partial thromboplastin time, ie., a reagent containing a phospholipid and a contact activator). Russel's viper venom (RVV time) can also be utilized as the procoagulant reagent. Contact activators utilized in the method of the invention as procoagulant reagents include micronized silica particles, ellagic acid, sulfatides, kaolin or the like known to those of skill in the art. Preferably, the procoagulant reagent is tissue factor or tissue thromboplastin. The procoagulant, such as tissue factor, may be a crude natural extract, for example, from rabbit brain or bovine brain, or may be a purified or recombinant tissue factor reagent. Optimal concentrations of the procoagulant reagent can be determined by those of skill in the art, depending on the reagent utilized.

The procoagulant reagent may intrinsically include phospholipid, such as that typically released from traumatized tissue, or in the case of purified or recombinant procoagulant reagent, phospholipid may be exogenously included in the test sample. One of skill in the art can readily identify a procoagulant phospholipid reagent. Such a phospholipid procoagulant reagent is preferably present at a concentration of about 5–100 µM, most preferably from about 10–50 µM, in the test sample.

Factor V deficient plasma included in the test sample can be obtained from a commercial source or by immunoadsorption of plasma with anti-FV antibodies, for example. The specimen, such as plasma, is preferably diluted, for example in a physiologically balanced buffer (e.g., Tris-buffered saline), before adding the test components. Preferably, when the test specimen is obtained from a subject receiving anticoagulant therapy at the time of the assay, such as heparin or warfarin, or from a subject with a lupus anticoagulant, the specimen is diluted. A preferred dilution is from about 1:2 to 1:300, and most preferably from about 1:6 to about 1:100. Most preferably, several dilutions of the test specimen are prepared and a dilution curve is obtained.

The method of the invention includes the addition of calcium to the test sample. Calcium (Ca2+) may be in the form of a plasma soluble salt that provides the Ca2+ ions in a free, uncomplexed form, i.e., strong Ca2+ chelators should be avoided. The final concentration of Ca2+ in the test sample is preferably from about 0.5 mM to 50 mM, and most preferably from about 5 mM to 5 mM.

Activated protein C (APC) as used in the method of the invention may be derived from a human or non-human source. The concentration of APC in the test sample is from about 10 ng/ml to 50 µg/ml, preferably from about 100 ng/ml to 10 µg/ml, and most preferably from about 200 ng/ml to 1 µg/ml.

The method of the invention is performed on a first test sample as described above, which includes APC, and a second test sample which does not include APC. Those of ordinary skill in the art can readily ascertain various ways in which the test sample preparation can be modified to produce the first and second test samples, such that two test samples are obtained which differ only by the presence or absence of APC. For example, a single initial test sample containing specimen, procoagulant reagent and factor V deficient plasma could be produced and to two separate aliquots of the initial sample are added either calcium or calcium plus APC. Alternatively, the preparation of a common initial test sample can be avoided and two parallel test samples prepared separately which differ only by the presence of APC.

The test samples are analyzed by measuring the clotting times of each of the samples and comparing them to each other and to normal reference interval values obtained for external standard samples (e.g., a normal subject not having or at risk of having a disorder as described herein). There are several methods for analyzing the results of the clotting times. For example, the difference between the clotting time for the test sample in the presence of APC and the test sample in the absence of APC can be determined and the results expressed as "clotting time difference". Clotting time difference is illustrated in the Examples. Briefly, test plasmas are diluted (e.g., 1:20, 1:40 and 1:80) in a physiological by balanced buffer (e.g., tTris buffered saline (TBS)) followed by addition of the appropriate reagents, to initiate clotting. Clotting times are determined and recorded, preferably as the average of duplicate samples. Preferably, each time the assay is performed, reference curves for each assay condition are prepared, for example, as log/log plots of clotting times against dilutions in buffer (i.e., 1:10 to 1:100) of pooled normal reference plasma.

The ratio between the clotting time of the test sample in the presence of APC and the test sample in the absence of APC can also be determined, and the results expressed as a ratio. In addition, the ratio of the clotting time of the test samples, as described above, can be determined in parallel with the ratio of the clotting time of a reference plasma. The ratios are normalized and compared to a standard plasma sample tested in the presence of an anticoagulant such as warfarin, for example, and to a standard normal plasma sample.

The comparison of clotting time described above is always determined with a standard value obtained for samples from normal individuals subjected to the identical test sample additions and under identical conditions as the test samples from the specimens being tested. The finding of a sample clotting time that is not normal compared to the standard value is taken as an indication of the subject suffering from the disorder or as being at risk for acquiring the disorder, in particular an enhanced clotting time is taken as an indication of a thrombotic disorder or a risk for acquiring such a disorder.

Specifically, a longer clotting time is observed in a normal test sample from a subject not having an APC-resistant factor V or Va disorder as described herein, as compared to a subject being heterozygous for the Arg506Gln (R506Q) mutation of factor V or Va. Similarly, a longer clotting time is observed for a subject with a heterozygous mutation as compared to a subject with a homozygous mutation. The length of time required for the blood to clot will depend on the concentration of coagulation factors, including the procoagulant reagent and factor V deficient plasma, calcium and APC, in other words, depending on the dilution of the test sample.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method.

The kit of the invention is useful for the diagnosis of a thrombotic disorder associated with activated protein C (APC) resistant factor V or Va in a subject having or at risk for having the disorder, the kit comprising carrier means being compartmentalized to receive in close confinement therein one or more containers comprising a first container containing a procoagulant reagent, a second container containing factor V deficient plasma, and a third container containing activated protein C (APC). Further containers may optionally contain a calcium reagent, such as CaCl2 or appropriate diluents for dissolving or diluting other reagents.

The following examples are intended to illustrate but not limit the invention. While they are typical of those that might be used, other procedures known to those skilled in the art may alternatively be used.

Example 1

Materials and Methods

1. Test Plasma Samples

Four and one-half ml of venous blood were collected into a siliconized BD Vacutainer tube containing 0.5 ml of 3.2% sodium citrate. Platelet poor plasma was prepared by centrifugation at 3,000 rpm for 15 minutes at room temperature.

Plasma samples were kept frozen in capped plastic tubes at −70° C. to −80° C. until tested.

Plasma was obtained from the following sources: (1) 39 asymptomatic volunteers from the staff of the Laboratory Service of UCSD Medical Center and the staff of a research laboratory; (2) 21 randomly selected patients receiving oral anticoagulant therapy with warfarin; (3) 29 patients receiving oral anticoagulant activity as determined from a combination of a) a prolonged APTT that failed to correct upon a 1:1 mix with normal plasma, b) increasing apparent coagulant activity with increasing dilution of the plasma in assays for factors VIII, IX, XI, and XII, and c) an abnormal dilute Russell's viper venom test; (4) 15 patients with known free protein S deficiency; (5) 21 patients with history of thrombosis and no evidence for a lupus anticoagulant or deficiency in antithrombin, protein C or protein S. The plasma samples had been stored frozen for periods varying from several days to several years.

2. Pooled Normal Reference Plasma

This plasma was prepared by pooling plasma obtained from venous blood collected in one tenth volume of a buffered citrate anticoagulant (0.06 mol/L sodium citrate plus 0.04 mol/L citric acid) from between 15 and 20 healthy donors. It was stored in small aliquots at 70° C. The prothrombin time and activated partial thromboplastin time of the plasma from each donor was within 2 standard deviations of he mean of the individual plasma samples from the donors used for the routine control pooled reference plasma of the Special Coagulation Laboratory of the UCSD Medical Center.

3. The Tissue Factor-Dependent FV Assay For APC Resistance

The assay is based upon measuring the clotting time of a diluted test plasma sample in one-stage FV assay that is activated with tissue factor and clotted with Ca2+ alone and with as Ca2+ plus APC. Test plasmas were diluted 1/20, 1/40 and 1/80 in Tris-buffered-saline, pH 7.5, containing 0.1% bovine serum albumin (rBS/BSA) and kept on ice. For each plasma dilution, four clotting cuvettes were prepared, each containing 40 μl of the diluted sample, 40 μl of reconstituted rabbit brain thromboplastin (Sigmna Diagnostic, St. Louis, Mo.) and 40 μl of reconstituted human immunoadsorbed FV deficient plasma (Baxter, Miami, Fla.). After incubation for 3 minutes at 37° C., clotting was initiated in two cuvettes with 40 p of warmed $CaCl_2$ containing 2.5 μg/ml APC (Enzyme Research Laboratories, South Bend, Ind.). Clotting times were determined with an ST-4 semi-automated coagulometer (Diagnostica Stago, Parsippani, N.J.) and were recorded as the average of the duplicate samples. For each test sample, the assay was performed initially at a 1/40 dilution, and then at a second dilution, either 1/20 or 1/80, as decided by the clotting time of the 1/40 dilution. When abnormal results were obtained, the test was performed at all three dilutions. On each day the assay was performed, reference curves for each assay condition were prepared as log/log plots of clotting times against 1/10 to 1/80 dilutions in TBS/BSA of the pooled normal reference plasma.

4. Detection Of FV R506Q Mutation By DNA Analysis

A lymphocyte-rich layer was obtained from 10 ml of venous blood collected in acid citrate dextrose by standard Hypaque gradient technique and stored as a cell pellet at −20° C. until used. Genomic DNA was extracted from the cell pellet with the DNA Extraction Kit (Bio-synthesis, Louisville, cTX) according to the manufacturer's instructions.

The 267-base pair (bp) fragment of FV containing the coding sequence for the amino acid Arg-506 was obtained by a modification of the polymnerase chain reaction (PCR) method of Bertina, et al., (Bertina, supra). The 100 μl PCR reaction mixture contained about 1 μg DNA, 20 pmol of each of the two primers, PR-6967 and PR99020 (Bertina, supra), 20 nmol of each of the four deoxynucleotide triphosphates, 10 μl 10X PCR buffer (Perkin-Elmer, Branchburg, N.J.), and 2.5 U of Taq polymerase (Gibco, Grand Island, N.Y.). The DNA was denatured at 97° C. for 2 minutes and subjected to 30 cycles of PCR in an automated DNA thermal cycler (Perkin Elmer Cetus, Branchburg, N.J.). Each cycle consisted of 1 minute denaturation at 95° C., 1 minute annealing at 55° C., and 1 minute extension at 72° C. Following the last cycle, extension was completed for 7 minutes at 72° C. The product was then all cooled to 4° C. and stored at −20° C. until further processing.

Purification of the PCR products were carried out by use -of the QlAquick Spin PCR purification kit (Qiagen, Chatsworth, Calif.) according to the manufacturer's instructions. Purified DNA was eluted in 15 μl of 10 mM Tris-Cl, 1 mM ethylene-diaminetetraacetic acid, pH 8.0 (TE buffer and 11 μl of the purified DNA were digested with Mnl I (Biolabs, Beverly, Mass.) according to the manufacturer's instructions. The whole digest was then subjected to electrophoresis on a 2% agarose gel (Bertina, supra).

Example 2

Standardization of the Analysis of Test Results

Figure 1B:
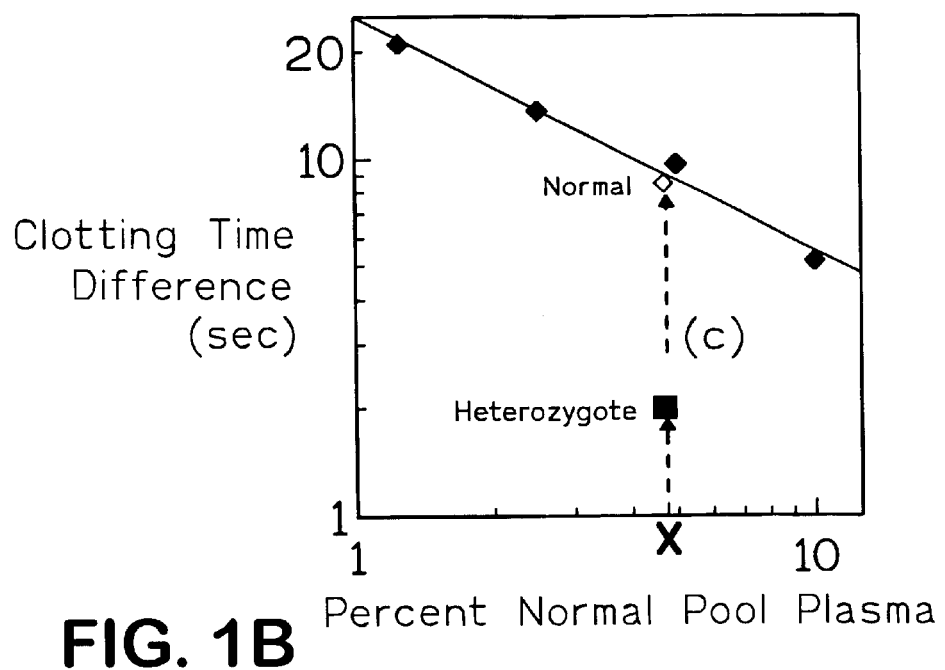
FIG. 1B shows a plot of the log of the difference in the clotting time obtained in the FV assay with and without APC against the log of percent concentration of pooled normal reference plasma. The lines in both plots are linear regression lines of the data. (♦) clotting time differences derived from data of FIG. 1A; (◇) hypothetical result from a normal subject; (■) hypothetical result from a heterozygous FV R506Q subject.

FIG. 1 shows primary and secondary plots obtained on FV assay with and without APC of dilutions of normal pooled reference plasma FIG. 1A shows reference curves obtained by plotting the log of clotting times against log of percent concentration of pooled normal reference plasma (primary plot) for the FV assay performed with (▲) and without (○) APC. (Y) a hypothetical clotting time obtained with a test sample which is converted to an equivalent dilution (X) of pooled normal reference plasma via steps (a) and (b). FIG. 1B shows a plot of the log of the difference in the clotting time obtained in the FV assay with and without APC against the log of percent concentration of pooled normal reference plasma. The lines in both plots are linear regression lines of the data. (♦) clotting time differences derived from data of FIG. 1A; (◇) hypothetical result from a normal subject; (■) hypothetical result from a heterozygous FV R506Q subject.

FIG. 1A provides and example of the reference curves obtained for the tissue factor-dependent FV assay (described in Example 1). As seen in this primary plot, the slope of the reference curve for the assay performed with APC was always greater than the slope of the assay performed with Ca2+ alone. Therefore, the log of the difference in clotting times between the FV assay with and without APC was plotted against the log of dilutions of pooled normal reference plasma (FIG. 1B). As seen in this secondary plot, the difference in clotting times increased from about 5 seconds to about 20 seconds as the dilution of the pooled normal reference plasma increased, i.e., as the concentration of FV in the test plasma decreased.

The following procedure was adopted to obtain a test result independent of both the basal level of FV in the test plasma and the dilution of the test plasma used in the assay:

(1) The clotting time of a dilution of a test plasma in the factor V assay without APC, denoted as Y on the y-axis of FIG. 1A, was located on the reference curve of that assay (step (a) of FIG. 1A) and converted into an equivalent dilution of pooled normal reference plasma, denoted as X on the abscissa of FIG. 1A (step (b) of FIG. 1A).

(2) The value for this equivalent dilution of pooled normal reference plasma was then located on the abscissa of the secondary plot (denoted as X on FIG. 1B). This was then used (step (c) of FIG. 1B) to delineate the clotting time difference due to APC that would be expected for this dilution of a normal test sample (e.g., (◇) of FIG. 1B). In a heterozygote for APC resistant FV R506Q, this difference should be unequivocally shorter than expected for normal plasma (e.g., (■) of FIG. 1B).

A single batch of APC, which was stored in small aliquots at −80° C. and thawed only once, was used to obtain the data presented here. The pooled normal plasma reference curves, prepared each day the assay was performed, yielded very similar primary and secondary plots. Therefore, for clarity of presentation of data, the clotting times obtained for primary and secondary plots on 10 different days were used to construct mean primary and secondary plots by linear regression. The results obtained with test samples on different days were analyzed in relation to these mean primary and secondary plots. In no instance did the use of these mean plots lead to a different interpretation of a test result than that derived from the use of same day reference plots.

Example 3

Test Results from Control Subjects

Figure 2A:
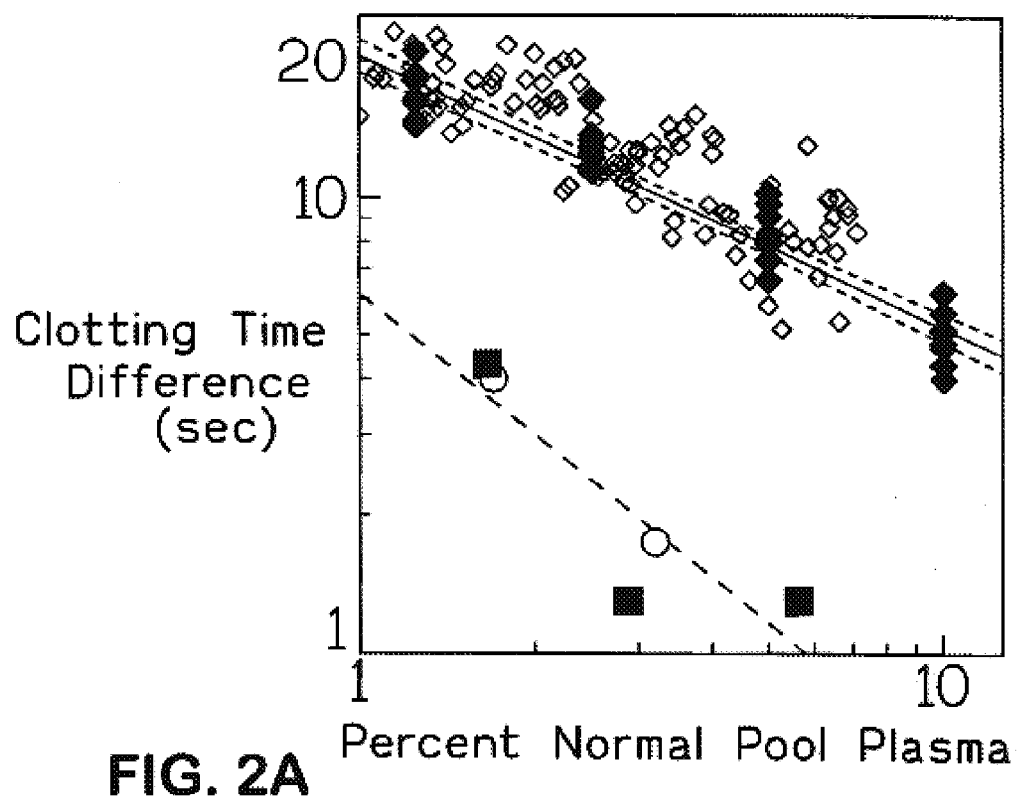
FIG. 2 shows secondary plot of results from 39 control subjects. A) clotting time differences obtained when the FV assay was performed with and without APC for dilutions of plasma from control subjects are plotted against their respective equivalent dilutions of pooled normal reference plasma. (♦) pooled normal reference plasma; (◇) 37 of the control subjects; (■, ○) two control subjects subsequently discovered to be heterozygotes for FV R506Q. Lower dashed line is regression line of the data obtained with dilutions of plasma from heterozygotes for FV R506Q. The mean regression line of the secondary plots obtained from assays of dilutions of pooled normal reference plasma on 10 different days is indicated by the solid line. The dotted lines delineate the 95% confidence limits of the slope of the mean regression lone. B) 2% agarose gel of the Mnl I digestion products of the PER-amplified 167-bp DNA fragment of FV from a normal control subject lane 3) and from the two control subjects with abnormal results shown in FIG. 1A (lanes 1 and 2). Lane 4 is the 100-bp DNA ladder standard.
Figure 2B:
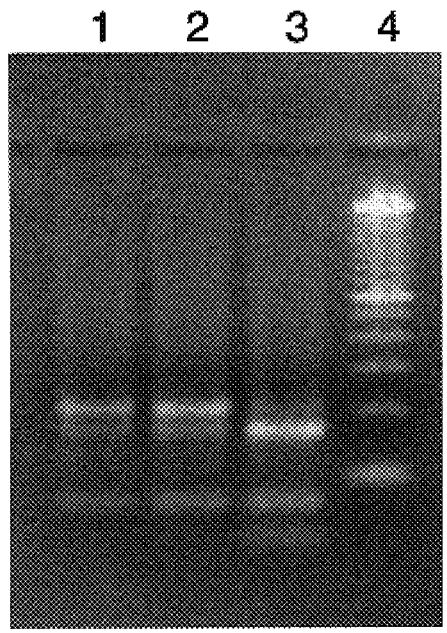

The clotting time differences obtained on performing FV assays with and without APC on two or three dilutions of each of the plasma samples obtained from 39 control subjects are illustrated in secondary plots FIG. 2A. FIG. 2A) clotting time differences obtained when the FV assay was performed with and without APC for dilutions of plasma from control subjects are plotted against their respective equivalent dilutions of pooled normal reference plasma. (♦) pooled normal reference plasma; (◇) 37 of the control subjects; (■, ○) two control subjects subsequently discovered to be heterozygotes for FV R506Q. Lower dashed line is regression line of the data obtained with dilutions of plasma from heterozygotes for FV R506Q. The mean regression line of the secondary plots obtained from assays of dilutions of pooled normal reference plasma on 10 different days is indicated by the solid line. The dotted lines delineate the 95% confidence limits of the slope of the mean regression line. FIG. 2B) 2% agarose gel of the Mnl I digestion products of the PCR-amplified 167-bp DNA fragment of FV from a normal control subject (lane 3) and from the two control subjects with abnormal results shown in FIG. 1A (lanes 1 and 2). Lane 4 is the 100-bp DNA ladder standard.

The clotting time differences obtained for 37 of the 39 control subjects are closely distributed around the regression line of the mean secondary plot. In contrast, plasma from two individuals yielded markedly shorter clotting time differences than expected for normal plasma (FIG. 2A, ■ and ○). Both of these individuals are in their thirties with no history of health problems. Subsequent DNA analysis confirmed that both of these subjects are heterozygotes for the FV R506Q mutation (FIG. 2B). As can be seen in FIG. 2B, Mnl I digestion of the normal DNA fragment yields a single band of 163-bp (lane 3), whereas Mnl I digestion of the DNA fragment from a FV R506Q heterozygote yields an additional band of 200-bp resulting from the loss of an Mnl I restriction site in the mutant FV molecule (lanes 1 and 2).

Example 4

Effect of Heparin Upon Test Results

Heparin, in a final concentration of 0.5 U/ml, was added to plasma from two of the normal control subjects and to plasma from the two above-described heterozygotes for the FV R506Q mutation. Clotting time differences at a 1/40 dilution of plasma from the two normal subjects were as follows: for plasma not containing heparin, 13.6 seconds and 14.5 seconds; for plasma containing heparin, 14.0 seconds and 16.0 seconds. The corresponding values for the two heterozygote subjects were 6.6 seconds and 8.3 seconds; and 7.9 seconds and 7.4 seconds, respectively. Thus, this plasma concentration of exogenous heparin, which exceeds the plasma level recommended for continuous intravenous therapy with heparin, did not alter the interpretation of test results.

Example 5

Test Results from Two Patients Homozygous for APC Resistant Factor V

Plasma samples were available from two patients who had been found earlier on DNA analysis to be homozygous for APC resistant FV. In contrast to the heterozygotes, in whom longer clotting time were always obtained in the FV assay with APC, plasma from these two homozygotes consistently yielded slightly shorter times in the FV assay with APC than in the FV assay without APC (Table 1).

TABLE 1

CLOTTING TIME DIFFERENCES OBTAINED IN THE FACTOR V ASSAY FOR TWO HOMOZYGOTES FOR APC RESISTANT FACTOR V

| | Clotting Time Difference (sec)* Dilution of Plasma | | |
|---|---|---|---|
| | 1/20 | 1/40 | 1/80 |
| Normal plasma | +7.0 | +11.0 | +19.5 |
| Homozygote 1 | −2.5 | −2.5 | −2.0 |
| Homozygote 2 | −3.0 | −2.5 | −0.5 |

*The clotting time in the factor V assay obtained without APC was subtracted from the clotting time in the factor V assay obtained with APC.

Example 6

Test Results from Patients Treated with Warfarin

Figure 3:
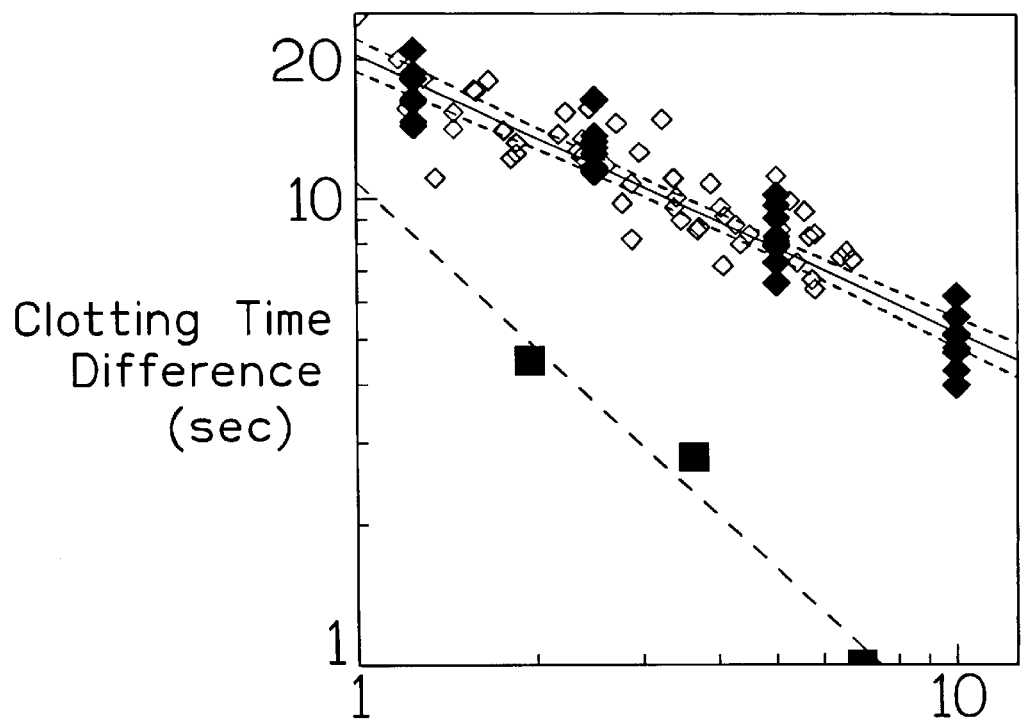
FIG. 3 shows secondary plot of results from 21 randomly selected patients receiving anticoagulant therapy with warfarin. (◇) 20 patients in whom the response to APC did not differ from normal (compare with FIG. 2A); (■) a patient later shown to be heterozygous for FV R506Q. Other symbols are as described in the legend to FIG. 2.

FIG. 3 shows secondary plot of results from 21 randomly selected patients receiving anticoagulant therapy with warfarin. (◇) 20 patients in whom the response to APC did not differ from normal (compare with FIG. 2A); (■) a patient later shown to be heterozygous for FV R506Q. Other symbols are as described for FIG. 2.

The clotting time difference obtained in the tissue factor-dependent FV assay for APC resistance with dilutions of plasma from 21 randomly selected patients receiving warfarin are shown in FIG. 3. In 20 of the 21 patients, these values were closely distributed around the regression line of the mean secondary plot. Dilutions of plasma from a single patient, who had experienced several episodes of deep vein thrombosis, yielded much shorter clotting time differences than expected for normal plasma. Subsequent DNA analysis of a blood sample from this patient revealed heterozygosity for the FV R506Q mutation.

Example 7

Test Results from Patents with Protein S Deficiency

Figure 4:
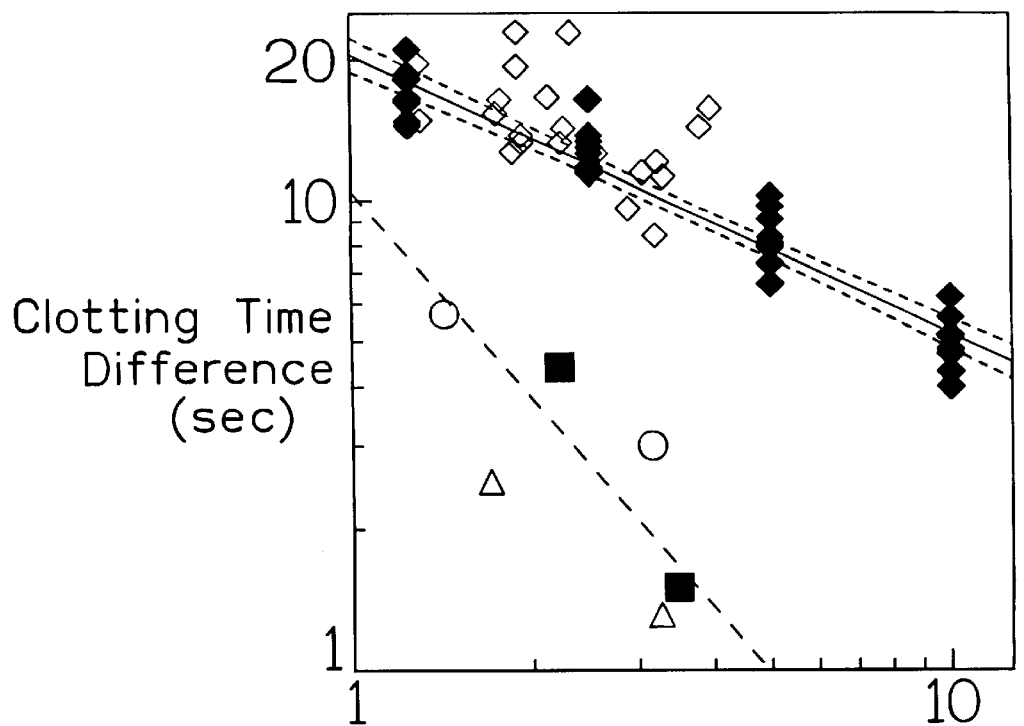
FIG. 4 shows secondary plot of results from 15 patients with free protein S deficiency. (◇) 13 patients in whom responses to APC did not differ from normal subjects; (■) a patient in whom the response to APC was consistent with heterozygosity for FV R506Q; a second heterozygote patient whole on (○) or off (○) warfarin therapy. Other symbols are as described in the legend to FIG. 2.

FIG. 4 shows secondary plot of results from 15 patients with free protein S deficiency. (◇) 13 patients in whom responses to APC did not differ from normal subjects; (■) a patient in whom the response to APC was consistent with heterozygosity for FV R506Q; a second heterozygote patient whole on (○) or off (○) warfarin therapy. Other symbols are as described in the legend to FIG. 2.

Stored plasma samples were available from 15 patients who had been found to have a deficiency of free protein S antigen by the Special Coagulation Laboratory at UCSD Medical Center. Plasma from 13 of these patients gave normal test results, whereas plasma from two patients yielded markedly shorter clotting time differences than expected for normal plasma In one of these patients, warfarin had been temporarily discontinued at the time the first sample was obtained and had been started again a the time a second sample was obtained. The data from both samples are shown in FIG. 4 and provide further evidence that therapy with warfarin does not affect the tissue factor-dependent FV assay for APC resistance. Subsequent DNA analysis in this patient confirmed heterozygosity for the FV R506Q mutation.

Example 8

Test Results from Patients with a Lupus Anticoagulant

Figure 5A:
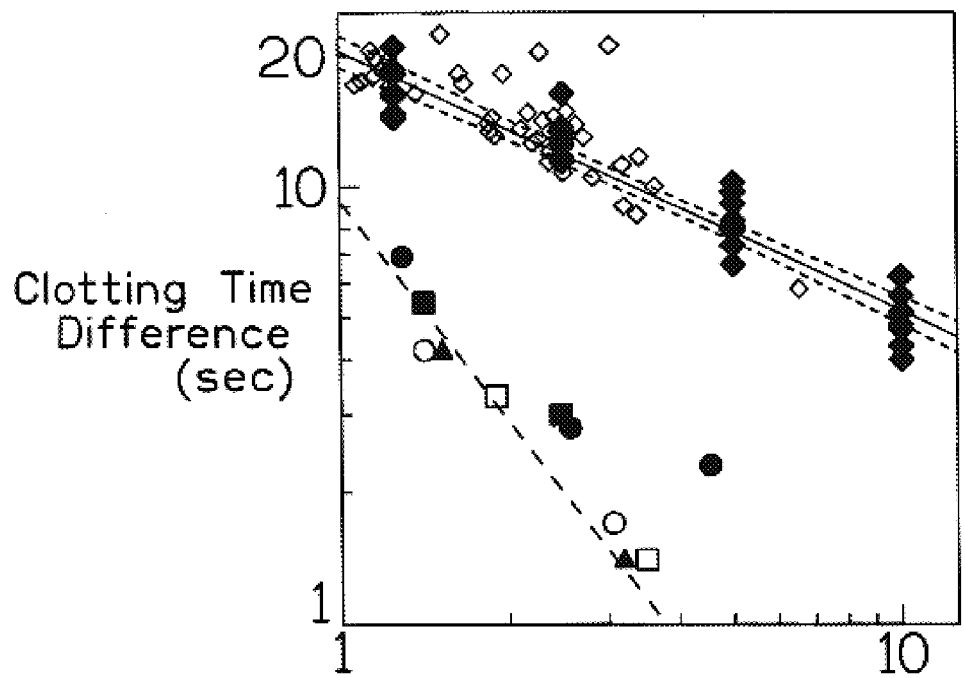
FIG. 5 shows secondary plot of results from 29 patients with a lupus anticoagulant. A) (◇) 24 patients in whom the response to APC did not differ from normal subjects normal. (○, ■, □, ▲, ●) patients in which the response to APC was consistent with heterozygosity for FV R506Q. Other symbols are as described in the legend of FIG. 2. B) Lane 1–3, DNA analysis of 3 heterozygotes from 4A: lane 4, a normal subject.
Figure 5B:
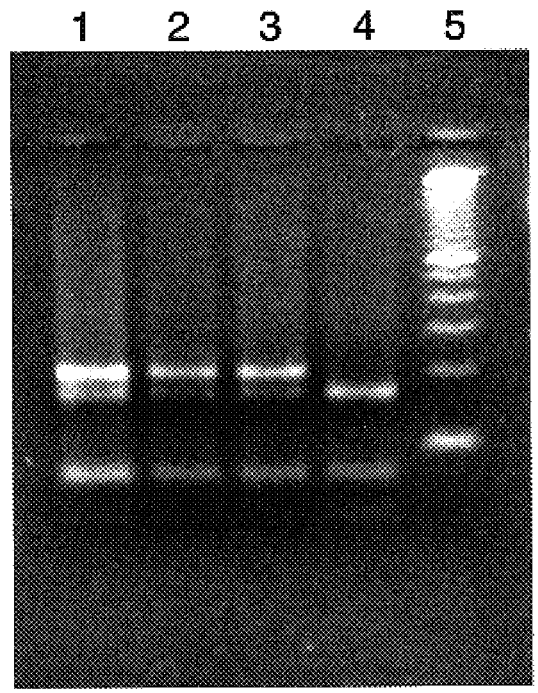

Twenty-nine patients with plasma lupus anticoagulant activity were tested for APC-resistant FV. FIG. 5 shows secondary plot of results from 29 patients with a lupus anticoagulant. A) (◇) 24 patients in whom the response to APC did not differ from normal subjects normal. (○, ■, □, ▲, ●) patients in which the response to APC was consistent with heterozygosity for FV R506Q. Other symbols are as described for FIG. 2. B) Lane 1-3, DNA analysis of 3 heterozygotes from 4A: lane 4, a normal subject In plasma from 24 patient the clotting time differences were similar to those expected for normal plasma. Twelve of these 24 patients had a history of thrombosis. In plasma from five patients, the clotting time differences were markedly shorter than those expected for normal plasma. Four of these patients had a history of thrombosis and at least two were receiving oral anticoagulant therapy with warfarin when tested. The patient without a history of thrombosis was over 90 years old when the discovery of a lupus anticoagulant on a routine pre-operative evaluation led us to test the plasma for APC resistant FV. Blood samples were available for DNA analysis from this patient and from two of the APC resistant patients with a history of thrombosis. All three patients were found to be heterozygotes for the FV R506Q mutation (FIG. 5B).

Example 9

Test Results from Patients with a History of Thrombosis and No Earlier Laboratory Evidence for an Increased Risk for Thrombosis Stored plasmas were available from 21 patients who had a history of significant thrombosis and earlier negative tests for a lupus anticoagulant or a deficiency of protein C, S, or antithrombin. FIG. 6 shows secondary plot of results from the 21 patients: A) (♦) pooled normal reference plasma; (◇) 11 patients in whom the response to APC did not differ from normal. All other symbols, seen in the lower left portion of the figure, denote cloning time differences obtained with two or more dilutions of plasma from 10 patients in whom the response to APC was consistent with heterozygosity for FV R506Q. B) Lane 1-4, DNA analysis of 4 of the 10 heterozygotes from 6A. Lane 5 shows the results for a normal subject.

Figure 6A:
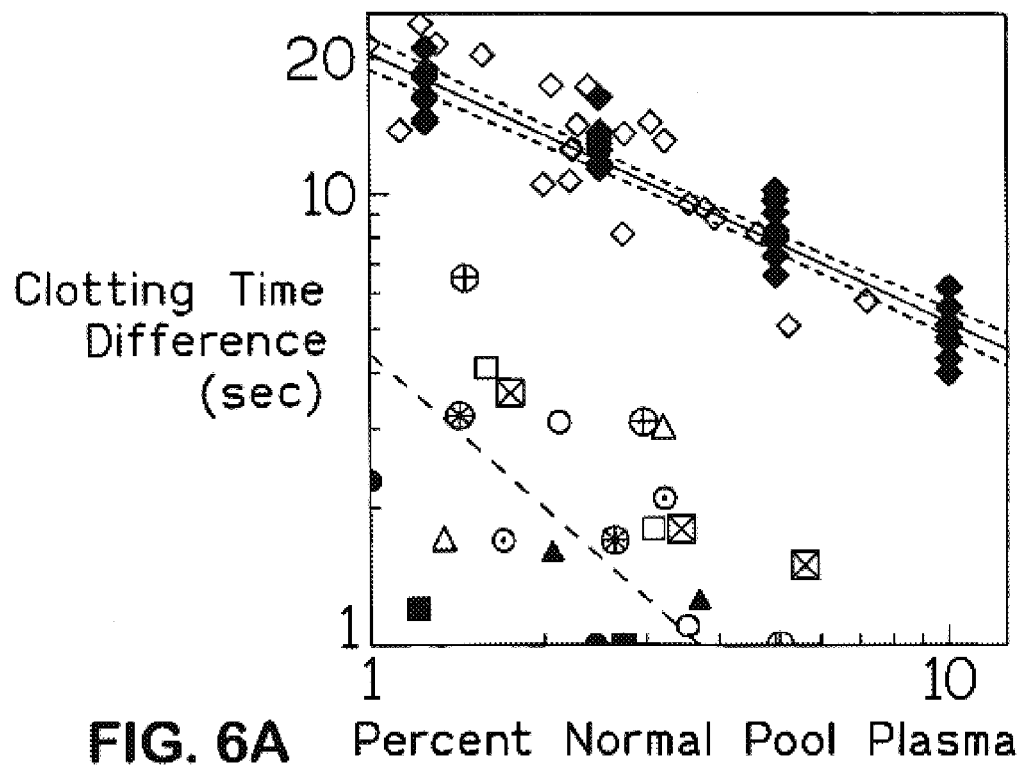
FIG. 6 shows a secondary plot of results from the 21 patients: A) (♦) pooled normal reference plasma; (◇) 11 patients in whom the response to APC did not differ from normal. All other symbols, seen in the lower left portion of the figure, denote clotting time differences obtained with two or more dilutions of plasma from 10 patients in whom the response to APC was consistent with heterozygosity for FV R506Q. B) Lane 1–4, DNA analysis of 4 of the 10 heterozygotes from 6A. Lane 5 shows the results for a normal subject.
Figure 6B:
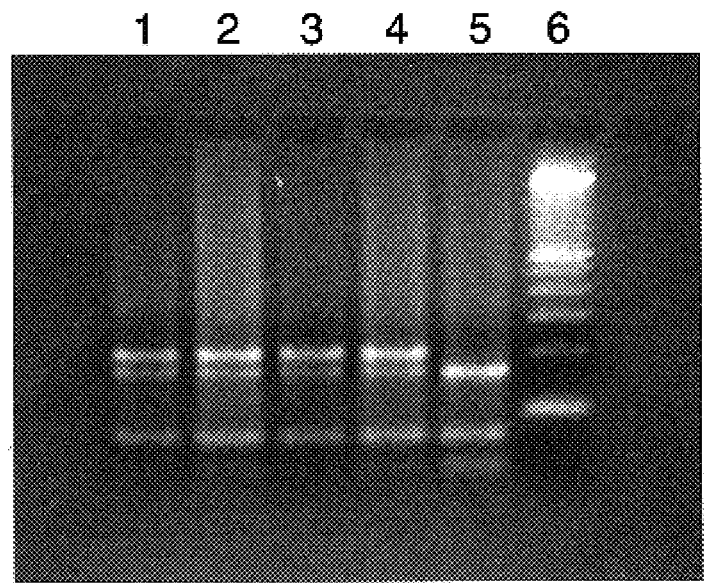

In 10 of these plasma, markedly shorter clotting time differences were found in response to APC than that expected for normal plasma (FIG. 6A). Four of these patients were available for DNA analysis and all four were found to be heterozygotes for the FV R506Q mutation (FIG. 6B).

The foregoing is meant to illustrate, but not to limit, the scope of the invention. Indeed, those of ordinary skill in the art can readily envision and produce further embodiments, based on the teachings herein, without undue experimentation.

What is claimed is:

1. An in vitro method for diagnosing a subject as having or as being at risk for having a thrombotic disorder associated with activated protein C (APC)-resistant factor V or Va, wherein the subject is presently on an oral anticoagulant regimen, the method comprising:
   a) contacting a test sample comprising a coagulation factor V or Va-containing specimen from the subject with a procoagulant reagent, factor V-deficient plasma to provide coagulation factors other than factors V or Va, calcium present in a concentration from about 5 mM to 15 mM, and APC present at from about 100 ng/ml to 10 ug/ml in a test reaction, wherein the test sample is initially diluted from 1/40 to 1/80; and
   b) comparing the clotting time for the test reaction to the clotting time for a control reaction carried out under the same conditions as the test reaction, but with a control sample comprising a coagulation factor V or Va-containing specimen from an individual not having or not at risk of having a thrombotic disorder associated with APC-resistant factor V or Va, wherein:
      i) detection of a decreased clotting time in the test reaction relative to the control reaction indicates a diagnosis of a thrombotic disorder associated with APC-resistant factor V or Va; and
      ii) detection of a similar clotting time in the test reaction relative to the control reaction indicates that the subject does not have or is not at risk of developing a thrombotic disorder associated with APC-resistant factor V or Va.

2. The method of claim 1, wherein the specimen from the subject is previously frozen plasma.

3. The method of claim 1, wherein the thrombotic disorder is thrombophilia.

4. The method of claim 1, wherein the thrombotic disorder is due to a factor V mutation.

5. The method of claim 4, wherein the mutation results in a change from arginine to glutamine at position 506 of factor V.

6. The method of claim 1, wherein the procoagulant reagent comprises tissue factor.

7. The method of claim 1, wherein the procoagulant reagent comprises a phospholipid.

8. The method of claim 7, wherein the phospholipid is present at a concentration of about 5–100 uM in the test reaction.

9. The method of claim 7, wherein the phospholipid is present at a concentration of about 10–50 uM in the test reaction.

10. The method of claim 1, wherein the procoagulant reagent comprises an activator of the intrinsic coagulation pathway.

11. The method of claim 10, wherein the activator is a clotting factor selected from the group consisting of factor Xa, factor IXa, factor XIa and factor XIIa.

12. The method of claim 1, wherein the procoagulant is a reagent selected from the group consisting of kallikrein, Russell's viper venom, micronized silica particles, ellagic acid, sulfatides, kaolin, and tissue thromboplastin.

13. The method of claim 1 wherein the specimen from the subject is diluted in a physiologically balanced buffer.

14. The method of claim 1, wherein the APC in the test reaction is present at from about 200 ng/ml to 1 ug/ml.

15. The method of claim 1, wherein the anticoagulant is warfarin.

16. The method of claim 1, further comprising setting up a no-APC test reaction, carried out under the same conditions as the test reaction except that no APC is added to the reaction, wherein a clotting time for the test reaction that is similar to, or faster than, a clotting time for the no-APC reaction is indicative of a subject having a thrombotic disorder associated with a homozygous mutation from arginine to glutamine at position 506 of factor V.

17. An in vitro method for diagnosing a subject as having or as being at risk for having a thrombotic disorder associated with activated protein C (APC)-resistant factor V or Va, wherein the subject is presently on an oral anticoagulant regimen, the method comprising:

a) contacting a test sample comprising a coagulation factor V or Va-containing specimen from the subject with a procoagulant reagent, factor V-deficient plasma to provide coagulation factors other than factors V or Va, calcium sufficient to initiate clotting, and APC, wherein the test sample is initially diluted from 1/40 to 1/80; and b) comparing the clotting time for the test reaction to the clotting time for a no-APC control reaction carried out under the same conditions as the test reaction, but without adding APC, wherein detection of a similar clotting time or faster clotting time in the test reaction relative to the no-APC control reaction indicates a diagnosis of a thrombotic disorder associated with APC-resistant factor V or Va.

18. The method of claim 17, wherein a clotting time for the test reaction that is faster than, a clotting time for the no-APC reaction is indicative of a subject having a thrombotic disorder associated with a homozygous mutation in factor V or Va rendering the factor APC-resistant.

19. The method of claim 18, wherein the mutation is a change from arginine to glutamine at position 506 of factor V.

* * * * *

UNITED STATES PATENT AND TRADEMARK OFFICE
CERTIFICATE OF CORRECTION

| | | |
|---|---|---|
| PATENT NO. | : 6,867,045 B1 | Page 1 of 1 |
| APPLICATION NO. | : 09/606779 | |
| DATED | : March 15, 2005 | |
| INVENTOR(S) | : Griffin et al. | |

It is certified that error appears in the above-identified patent and that said Letters Patent is hereby corrected as shown below:

Col. 1, line 5

Second Paragraph, Add --This invention was made with Government support under Grant Nos. HL 27234, HL 31950, and HL 21544 from the National Institutes of Health. The Government has certain rights in this invention.--

Signed and Sealed this

Twelfth Day of September, 2006

JON W. DUDAS
*Director of the United States Patent and Trademark Office*